United States Patent
Reif et al.

(10) Patent No.: US 9,963,668 B2
(45) Date of Patent: May 8, 2018

(54) COMBINED FILTER

(71) Applicant: Sartorius Stedim Biotech GmbH, Goettingen (DE)

(72) Inventors: Oscar-Werner Reif, Hannover (DE); Gerhard Greller, Goettingen (DE); Paschalis Nikoloudis, Goettingen (DE); Ralf Lausch, Goettingen (DE); Ute Husemann, Goettingen (DE); Thomas Loewe, Goettingen (DE); Thomas Friese, Goettingen (DE); Thomas Dreher, Goettingen (DE)

(73) Assignee: Sartorius Stedim Biotech GmbH (DE)

( * ) Notice: Subject to any disclaimer, the term of this patent is extended or adjusted under 35 U.S.C. 154(b) by 223 days.

(21) Appl. No.: 14/425,330

(22) PCT Filed: Jul. 16, 2013

(86) PCT No.: PCT/EP2013/002103
§ 371 (c)(1),
(2) Date: Mar. 3, 2015

(87) PCT Pub. No.: WO2014/040669
PCT Pub. Date: Mar. 20, 2014

(65) Prior Publication Data
US 2015/0232799 A1    Aug. 20, 2015

(30) Foreign Application Priority Data

Sep. 12, 2012 (DE) .......... 10 2012 017 972

(51) Int. Cl.
*C12M 1/00* (2006.01)
*B01D 46/00* (2006.01)
(Continued)

(52) U.S. Cl.
CPC ......... *C12M 29/04* (2013.01); *B01D 46/0023* (2013.01); *B01D 53/22* (2013.01);
(Continued)

(58) Field of Classification Search
CPC .......... B01D 2053/221; B01D 2325/02; B01D 2325/38; B01D 46/0023; B01D 53/22;
(Continued)

(56) References Cited

U.S. PATENT DOCUMENTS

| 5,480,610 A | 1/1996 | Birkholz |
| 6,576,033 B1 | 6/2003 | Booth |

(Continued)

FOREIGN PATENT DOCUMENTS

| JP | 5-161827 | 6/1993 |
| JP | H05161827 A | 6/1993 |

(Continued)

OTHER PUBLICATIONS

Translation International Preliminary Report on Patentability and Written Opinion.

(Continued)

*Primary Examiner* — Nathan A Bowers
*Assistant Examiner* — Lydia Edwards
(74) *Attorney, Agent, or Firm* — Gerald E. Hespos; Michael J. Porco; Matthew T. Hespos

(57) ABSTRACT

The invention relates to a device for culturing cells in a bioreactor, the waste-air line of which leading out of the reactor interior comprises a waste-air filter having a sterile-filtration microfilter membrane, wherein at least one prefilter having a hydrophobic filter material is placed upstream of the waste-air filter toward the reactor interior.

13 Claims, 3 Drawing Sheets

(51) Int. Cl.
*B01D 53/22* (2006.01)
*B01D 71/36* (2006.01)
*C12M 1/12* (2006.01)

(52) U.S. Cl.
CPC .............. *B01D 71/36* (2013.01); *C12M 29/20* (2013.01); *C12M 37/02* (2013.01); *B01D 2053/221* (2013.01); *B01D 2325/02* (2013.01); *B01D 2325/38* (2013.01)

(58) Field of Classification Search
CPC ....... B01D 71/36; C12M 29/04; C12M 29/20; C12M 37/02
See application file for complete search history.

(56) References Cited

U.S. PATENT DOCUMENTS

| | | |
|---|---|---|
| 6,746,504 B2 | 6/2004 | Booth |
| 2003/0041572 A1* | 3/2003 | Lohr ................. B01D 46/0024 55/385.2 |
| 2003/0200738 A1* | 10/2003 | Booth ................. B01D 46/002 55/485 |
| 2007/0029256 A1 | 2/2007 | Nakano |
| 2010/0282083 A1* | 11/2010 | Edwards ............ B01D 46/0028 95/285 |
| 2011/0076759 A1 | 3/2011 | Reif et al. |
| 2013/0323781 A1 | 12/2013 | Moularat et al. |

FOREIGN PATENT DOCUMENTS

| | | |
|---|---|---|
| JP | H05337169 A | 12/1993 |
| JP | 2002058730 A | 2/2002 |
| JP | 2002531235 A | 9/2002 |
| JP | 2006223207 A | 8/2006 |
| JP | 2009157109 A | 7/2009 |
| WO | 2005014149 A1 | 2/2005 |
| WO | 2012069752 A1 | 5/2012 |

OTHER PUBLICATIONS

International Search Report dated Sep. 17, 2013.
Japanese Office Action dated Mar. 1, 2016.
Japanese Office Action dated Jan. 19, 2017.

* cited by examiner

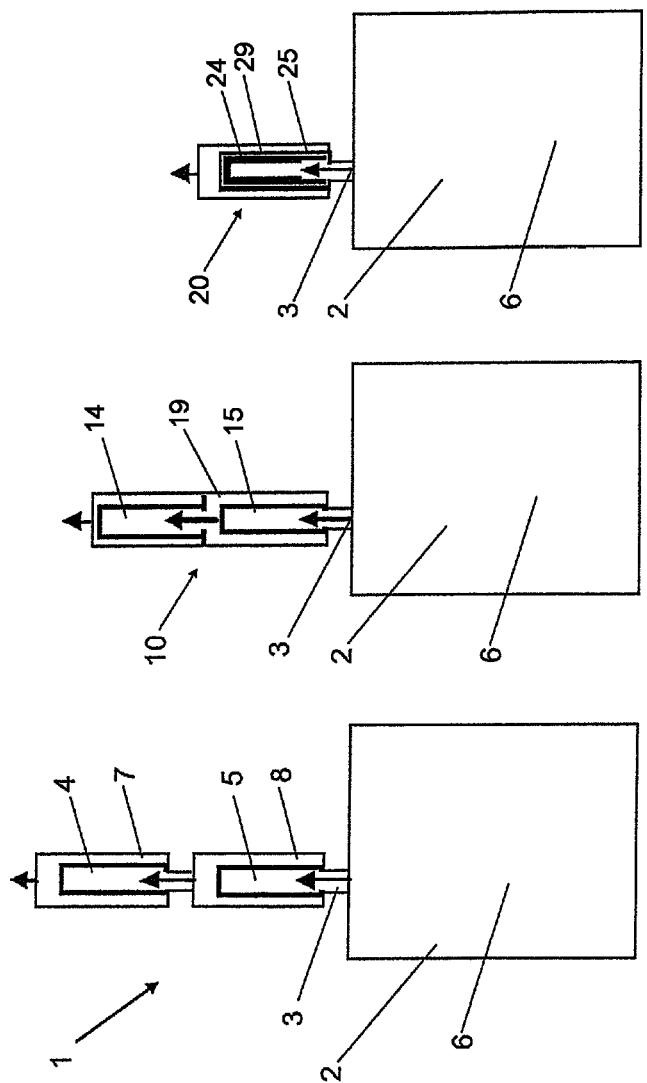

COMBINED FILTER

BACKGROUND

Field of the Invention

The invention relates to a device for culturing cells in a bioreactor, the waste-air line of which leading out of the reactor interior comprises a waste-air filter having a sterile-filtration microfilter membrane.

Description of the Related Art

In order to culture cells in a bioreactor, a relatively large air flow must be reliably supplied to and discharged from the reactor interior forming a closed culture chamber. While this is done, cells (e.g. microorganisms) must be held back both from the outside to the inside and from the inside to the outside. The reactor interior or the culture chamber is generally operated under elevated temperature with an aerated aqueous solution containing nutrients and cells (e.g. microorganisms) to be propagated.

According to the prior art, hydrophobic sterile-filtration microfilter membranes which are, for example, qualified in accordance with ASTM 838-05 are used. Preferably, said membranes are hydrophobic to the extent that, firstly, no water penetrates into the filter membrane structure and, secondly, no closed water film can form on the filter membrane surface and thereby restrict or stop the air flow through the filter membrane. If water vapor is carried out of the solution with the air flow, it condenses at least in part on the filter membrane and all housing and pipeline parts and must be discharged. At high air flows in particular, cells, cell debris or particulate substances, for example nutrients or residues thereof, are carried along onto the filter membrane surface and block the pore structure of the filter membrane.

DE 10 2008 025 968 A1 discloses a device for culturing cells in a bioreactor, the waste-air line of which leading out of the reactor interior comprises a hydrophobic sterile filter or waste-air filter having a microfilter membrane. In order to avoid the condensation of water vapor on the filter membrane, a condenser is placed upstream of the waste-air filter in the case of the known bioreactor, which condenser cools down warm moist waste air and recycles dripping water into the reactor interior. Although this was fundamentally proven to be effective, it is relatively cost-intensive and cannot prevent cells, cell debris or particulate substances from being carried onto the filter membrane surface and blocking said surface.

It is an object of the present invention to improve the known device for culturing cells to the extent that it, firstly, can be produced cost-effectively and that it, secondly, in addition to avoiding a blockage by water vapor, also prevents a blockage of the microfilter membrane by cells or particulate substances.

SUMMARY OF THE INVENTION

This object is achieved in that at least one prefilter having a hydrophobic filter material is placed upstream of the waste-air filter toward the reactor interior.

By using a hydrophobic filter material as prefilter, the sterile-filtration microfilter is protected in a simple and cost-effective manner from an unwanted blockage by both water vapor or water and cells, cell debris or particulate substances.

Preferred embodiments are the subject matter of the dependent claims.

In a preferred embodiment of the invention, the prefilter and the waste-air filter form a joint combination filter and are in particular arranged in a joint housing. In said housing, the prefilter and the waste-air filter are designed as two separate filter inserts arranged in succession in the housing. However, it is also possible to arrange the filter material of the prefilter directly on the microfilter membrane to be protected of the waste-air filter. Thus, the prefilter can, for example, be arranged coaxially in relation to the waste-air filter in the housing.

In principle, it is also possible to insert the combination filter into an inflow line to the bioreactor.

In a further preferred embodiment of the invention, the filter material is designed as a glass fiber filter. However, it is also possible to form the filter material of the prefilter from melt-blown fiber filter materials composed of PE (polyethylene), PP (polypropylene), PET (polyethylene terephthalate), PESU (polyethersulfone), PVDF (polyvinylidene fluoride) or PMP (polymethylpentene). Melt-blown is understood by a person skilled in the art to mean a process in which nonwoven fabrics or nonwovens are produced directly from granules. In said process, a specific spinning procedure is used in combination with high-speed hot air in order to produce finely fibrous fabrics having different structures.

In a further preferred embodiment of the invention, the filter material of the prefilter has a mean pore size of greater than 0.1 µm and smaller than 100 µm. More preferably, the mean pore size can be between 3 µm and 30 µm. More particularly, the mean pore size can be between 10 µm and 15 µm.

In a further preferred embodiment of the invention, the filter material of the prefilter has a thickness of from 50 µm to 250 µm.

In a further preferred embodiment of the invention, the waste-air filter has a hydrophobic microfilter membrane composed of PVDF (polyvinylidene fluoride), ePTFE (expanded polytetrafluoroethylene), PP or PE.

In a further preferred embodiment of the invention, the waste-air filter has a hydrophobic microfilter membrane.

In said embodiment, the hydrophobic microfilter membrane can be formed from a hydrophobic polymeric material, with both the membrane matrix and its inner and outer surfaces being hydrophobic. The aforementioned polymeric materials are preferably selected from the group comprising PVDF, PTFE (polytetrafluoroethylene), PMP, PP, PE or combinations thereof. In a further preferred embodiment, the membrane matrix is hydrophilic, whereas its inner and outer surfaces have hydrophobic properties as a result of coating or graft polymerization.

In a further preferred embodiment of the invention, the waste-air filter has a hydrophobic microfilter membrane having pore sizes of greater than 0.1 µm, preferably 0.2 µm.

Further features and advantages of the invention are revealed by the following specific description and the drawings.

BRIEF DESCRIPTION OF THE DRAWINGS

FIG. 1 a diagram of a device for culturing cells in a bioreactor having a waste-air filter and a prefilter arranged in separate housings.

FIG. 2 a diagram of a device for culturing cells in a bioreactor having a waste-air filter and a prefilter arranged as a combination filter in a joint housing.

FIG. 3 a diagram of a device for culturing cells in a bioreactor having a waste-air filter and a prefilter arranged as a combination filter in a joint housing, wherein the filter material of the prefilter rests directly on the microfilter membrane to be protected of the waste-air filter.

DETAILED DESCRIPTION

Figure 4:
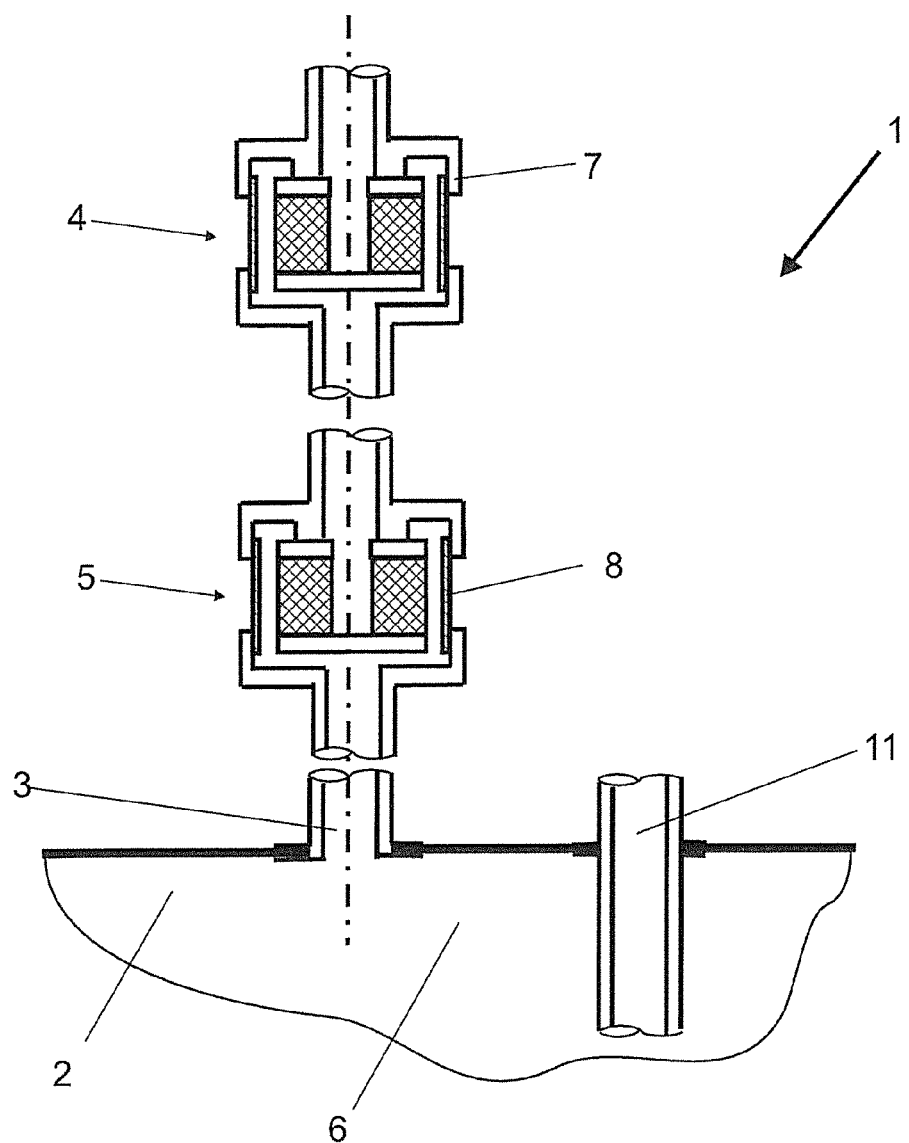
FIG. 4 a sectional and detailed side view of a further device according to FIG. 1.

A device 1 for culturing cells essentially consists of a bioreactor 2, a waste-air line 3, a waste-air filter 4 and a prefilter 5.

The bioreactor 2 has a reactor interior 6 which is connected to the waste-air filter 4 via the waste-air line 3. The prefilter 5 is placed upstream of the waste-air filter 4 toward the reactor interior 6.

In FIGS. 1 and 4, the waste-air filter 4 is arranged in a waste-air filter housing 7 and the prefilter 5 in a prefilter housing 8.

In FIG. 2, the waste-air filter 14 and the prefilter 15 are arranged in a joint filter housing 19 and form a joint combination filter 10.

Figure 5:
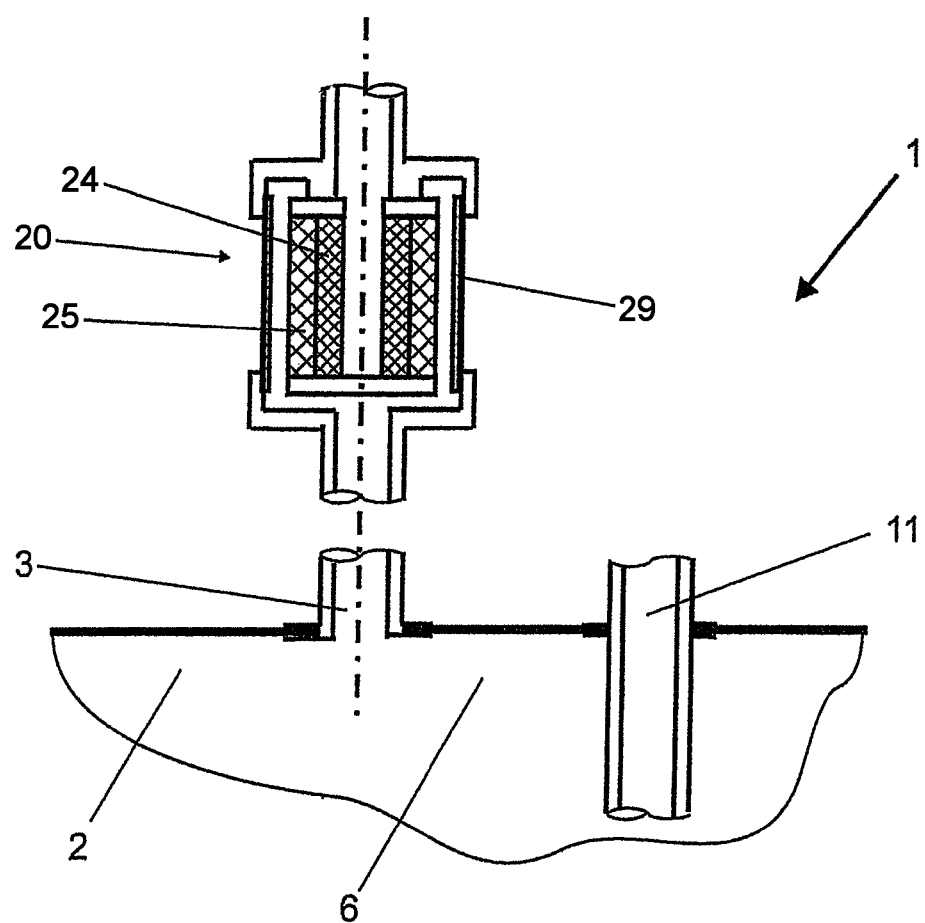
FIG. 5 a sectional and detailed side view of a further device according to FIG. 3, in which the filter material of the prefilter surrounds the microfilter membrane of the waste-air filter in a concentric manner.

In FIGS. 3 and 5, the prefilter 25 is arranged concentrically in relation to the waste-air filter 24, and so the prefilter 25 covers the waste-air filter 24. The combination filter 20 is, with its prefilter 25 and its waste-air filter 24, arranged in the joint filter housing 29.

The prefilters 5, 15, 25 have a mean pore size of between 10 and 15 µm. The filter material of the prefilters 5, 15, 25 has a thickness of from 50 to 250 µm. The hydrophobic microfilter membrane of the waste-air filter 14, 24 has a pore size of 0.2 µm in the exemplary embodiment.

The bioreactor 2 has, toward its reactor interior 6, a gas supply channel 11 via which gas can be supplied.

The following exemplary embodiments have been successfully tested:
Corresponding to the Exemplary Embodiment of FIG. 1:
Prefilter 5: one ply 10-15 µm prefilter material, pleated cartridge/capsule 1: BH9 capsule, 1 ply PP melt-blown filter material, mean flow pore size 10-15 µm (Topas), thickness 150 µm, basis weight 20 g/m²
Waste-air filter 4: Sartofluor sterile filter, pleated cartridge/capsule 2: BH9 capsule, 1 ply ePTFE microfilter membrane 0.2 µm
Combination Filter 20 Corresponding to the Exemplary Embodiment of FIGS. 3 and 5 (1 Ply 10-15 µm Prefilter Material Before 1 Ply ePTFE Microfilter Membrane 0.2 µm):
Prefilter 25: Pleated cartridge/capsule: BH9 capsule, 1 ply PP melt-blown filter material, mean flow pore size 10-15 µm (Togas), thickness 150 µm, basis weight 20 g/m² (before waste-air filter)
Waste-air filter 24: 1 ply ePTFE microfilter membrane 0.2 µm Assessment: functional, especially simple construction, very small dimensions, very simple operation, identical to operation without prefilter.

Needless to say, the embodiments discussed in the specific description and shown in the figures are only illustrative exemplary embodiments of the present invention. In the light of this disclosure, a person skilled in the art is provided with a broad spectrum of possible variations. More particularly, the filters 4, 14, 24, 5, 15, 25 or the combination filters 10, 20 can also be additionally arranged in the gas supply channel 11. It is also possible to place upstream of the combination filter 10, 20 a condenser (not further shown) toward the reactor interior 6.

LIST OF REFERENCE SIGNS

1 Device
2 Bioreactor
3 Waste-air line
4, 4', 4" Waste-air filter
5, 5', 5" Prefilter
6 Reactor interior
7 Waste-air filter housing
8, 8" Prefilter housing
9, 9" Filter housing
10, 10" Combination filter
11 Gas supply channel

The invention claimed is:

1. A device for culturing cells in a bioreactor, comprising:
a waste-air line leading up and out of a reactor interior of the bioreactor and to a location outside the bioreactor;
a waste-air filter in the waste-air line and having a sterile-filtration microfilter membrane; and
at least one prefilter between the waste-air filter and the reactor interior so that the prefilter is at a position in the waste-air line upstream of the waste-air filter with respect to a flow direction of waste air from the reactor interior of the bioreactor, the prefilter having a hydrophobic filter material formed from glass fiber filter materials or melt-blown fiber filter materials composed of PE, PP, PET, PESU, PVDx or PMP, and the filter material of the prefilter has a mean pore size of greater than 0.1 µm and smaller than 100 µm.

2. The device of claim 1, wherein
the prefilter and the waste-air filter form a joint combination filter.

3. The device of claim 2, wherein
the filter material of the prefilter rests directly on the microfilter membrane to be protected of the waste-air filter.

4. The device of claim 1, wherein
the filter material of the prefilter is a glass fiber filter.

5. The device of claim 1, wherein
the filter material of the prefilter has a mean pore size of greater than 3 µm and smaller than 30 µm.

6. The device of claim 5, wherein
the filter material of the prefilter has a mean pore size of from 10 to 15 µm.

7. The device of claim 1, wherein
the filter material of the prefilter has a thickness of from 50 to 250 µm.

8. The device of claim 1, wherein
the waste-air filter has a hydrophobic microfilter membrane composed of PVDF, ePTFE, PP or PE.

9. The device of claim 1, wherein
the waste-air filter has a hydrophobic microfilter membrane.

10. The device of claim 1, wherein
the waste-air filter has a hydrophobic microfilter membrane having a pore size of greater than 0.1 µm.

11. The device of claim 1, wherein the waste-air filter and the prefilter are disposed in a joint filter housing with the waste-air filter and the prefilter being aligned with one another along an axis of the waste-air line.

12. The device of claim 1 wherein the waste-air filter is arranged in a waste-air filter housing, and the prefilter is in a prefilter housing spaced from the waste-air filter housing.

13. The device of claim 1 wherein the prefilter is disposed relative to the bioreactor to permit a gravitational flow of condensate from the prefilter to the reactor interior of the bioreactor.

* * * * *